US00PP15996P2

(12) United States Plant Patent
Konst

(10) Patent No.: US PP15,996 P2
(45) Date of Patent: Sep. 27, 2005

(54) ***ALSTROEMERIA* PLANT NAMED 'KOSERIN'**

(50) Latin Name: *Alstroemeria hybrida*
Varietal Denomination: Koserin

(75) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 56 days.

(21) Appl. No.: 10/949,945

(22) Filed: Sep. 24, 2004

(51) Int. Cl.[7] ..... A01H 5/00
(52) U.S. Cl. ..... Plt./309
(58) Field of Search ..... Plt./309

*Primary Examiner*—Kent Bell
(74) *Attorney, Agent, or Firm*—C. A. Whealy

(57) ABSTRACT

A new and distinct cultivar of *Alstroemeria* plant named 'Koserin', characterized by its compact and mounded growth habit; pink and yellow-colored flowers; and good postproduction longevity.

2 Drawing Sheets

Botanical classification/cultivar designation: *Alstroemeria hybrida* cultivar Koserin.

BACKGROUND OF THE INVENTION

The present Invention relates to a new and distinct cultivar of *Alstroemeria* plant, botanically known as *Alstroemeria hybrida,* commercially used as a container-grown *Alstroemeria,* and hereinafter referred to by the name 'Koserin'.

The new *Alstroemeria* is a product of a planned breeding program conducted by the Inventor in Nieuwveen, The Netherlands. The objective of the breeding program was to develop new compact container-grown *Alstroemeria* cultivars with an early and freely flowering habit, attractive flower colors and excellent postproduction longevity.

The new *Alstroemeria* originated from a cross-pollination made by the Inventor in Nieuwveen, The Netherlands, of a proprietary *Alstroemeria hybrida* selection identified as 3148-3, not patented, as the female, or seed, parent with a proprietary *Alstroemeria hybrida* selection identified as 90-3-8, not patented, as the male, or pollen, parent. The new *Alstroemeria* was discovered and selected by the Inventor as a flowering plant within the progeny of the stated cross-pollination in a controlled environment in Nieuwveen, The Netherlands on Oct. 14, 1998.

Asexual reproduction of the new cultivar by root divisions taken in a controlled environment in Nieuwveen, The Netherlands, since Oct. 14, 1998, has shown that the unique features of this new *Alstroemeria* are stable and reproduced true to type in successive generations of asexual propagation.

SUMMARY OF THE INVENTION

Plants of the cultivar Koserin have not been observed under all possible environmental conditions. The phenotype may vary somewhat with variations in environment such as temperature and light intensity without, however, any variance in genotype.

The following traits have been repeatedly observed and are determined to be the unique characteristics of 'Koserin'. These characteristics in combination distinguish 'Koserin' as a new and distinct cultivar:

1. Compact and mounded growth habit.
2. Pink and yellow-colored flowers.
3. Good postproduction longevity.

Plants of the new *Alstroemeria* can be compared to plants of the parent selections. In side-by-side comparisons conducted in Nieuwveen, The Netherlands, plants of the new *Alstroemeria* differed from plants of the parent selections in growth habit as plants of the parent selections were not as compact as plants of the new *Alstroemeria.* In addition, plants of the new *Alstroemeria* and the parent selections differed in flower coloration.

Plants of the new *Alstroemeria* can also be compared to plants of the cultivar California, not patented. In side-by-side comparisons conducted in Nieuwveen, The Netherlands, plants of the new *Alstroemeria* differed from plants of the cultivar California in the following characteristics:

1. Plants of the new *Alstroemeria* were much more compact than and not as upright as plants of the cultivar California.
2. Plants of the new *Alstroemeria* had smaller leaves than plants of the cultivar California.
3. Plants of the new *Alstroemeria* had smaller inflorescences and smaller flowers than plants of the cultivar California.
4. Plants of the new *Alstroemeria* and the cultivar California differed in flower coloration as plants of the cultivar California had solid yellow-colored flowers.

BRIEF DESCRIPTION OF THE PHOTOGRAPHS

The accompanying colored photographs illustrate the overall appearance of the new *Alstroemeria*, showing the colors as true as it is reasonably possible to obtain in colored reproductions of this type. Colors in the photographs may differ slightly from the color values cited in the detailed botanical description which accurately describe the colors of the new *Alstroemeria.*

The photograph on the first sheet comprises a side perspective view of a typical flowering plant of 'Koserin' grown in a container.

The photograph on the second sheet is a close-up view of a typical flower of 'Koserin'.

DETAILED BOTANICAL DESCRIPTION

The aforementioned photographs, following observations and measurements describe plants of the new *Alstroemeria* grown in 33-cm containers in Nieuwveen, The Netherlands in a glass-covered greenhouse for 19 weeks and then grown in an outdoor nursery for four weeks. During the production of the plants, day temperatures ranged from 9 to 35° C. and night temperatures ranged from 2 to 16° C. Plants used for the photographs and description were about 23 weeks old. The photographs and the description were taken during the early summer. Color references are made to The Royal Horticultural Society Colour Chart, 1995 Edition, except where general terms of ordinary dictionary significance are used.

Botanical classification: *Alstroemeria hybrida* cultivar Koserin.

Parentage:

*Female parent.*—Proprietary *Alstroemeria hybrida* selection identified as 3148-3, not patented.

*Male parent.*—Proprietary selection of *Alstroemeria hybrida* identified as 90-3-8, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 5.1 cm. Diameter: About 6 mm. Texture: Smooth. Color: 161C.

Plant description:

*Plant habit.*—Compact and mounded; upright and outwardly spreading; freely basal branching, bushy appearance. Vigorous growth habit.

*Plant height.*—About 26 cm.

*Plant diameter* (*spread*).—About 43 cm.

*Flowering stem description.*—Aspect: Mostly upright to somewhat outwardly spreading. Length: About 26 cm. Internode length: About 2.4 cm. Strength: Strong. Texture: Glabrous, smooth. Color: Towards the base, 200A, with spots, 140D; towards the apex, 146B.

*Foliage description.*—Length, largest: About 6.6 cm. Width, largest: About 2 cm. Shape: Lanceolate. Apex: Acute. Base: Attenuate; sessile. Margin: Entire. Texture, upper and lower surfaces: Smooth, glabrous. Venation pattern: Parallel. Color: Developing foliage, upper surface: 138A. Developing foliage, lower surface: 138B. Fully expanded foliage, upper surface: 137A. Fully expanded foliage, lower surface: 137C. Venation, upper surface: 145A. Venation, lower surface: 138A.

Flower description:

*Flower type and habit.*—Single cup-shaped flowers arranged in compound umbels. Flowers face upright to outwards. Perianth segments separate. Freely and continuously flowering. Flowers not persistent.

*Natural flowering season.*—Flowering continuous from late spring to the fall in The Netherlands.

*Fragrance.*—None detected.

*Flower longevity on the plant.*—About one to three weeks.

*Flower longevity as a cut flower.*—About one to two weeks.

*Flower buds* (*showing color*).—Length: About 3.4 cm. Diameter: About 1.1 cm. Shape: Ovoid. Color: 48A; towards the apex, 138A.

*Umbel height.*—About 11.4 cm.

*Umbel diameter.*—About 12.8 cm.

*Number of flowers per umbel.*—About 3 to 8.

*Flower height.*—About 5.5 cm.

*Flower diameter.*—About 4.2 cm.

*Perianth.*—Arrangement: Six arranged in two whorls, each whorl with two lateral and one median segments. Size, inner perianth segments: Length, lateral segments: About 5.8 cm. Length, median segment: About 4.8 cm. Width, lateral segments: About 1.5 cm. Width, median segment: About 1.6 cm. Size, outer perianth segments: Length, lateral segments: About 4.8 cm. Length, median segment: About 5.5 cm. Width, lateral segments: About 2 cm. Width, median segment: About 2.5 cm. Shape, inner perianth, all segments: Lanceolate. Shape, outer perianth, all segments: Obovate. Apex, inner perianth, all segments: Acute; mucronate. Apex, outer perianth, all segments: Bracket-shaped. Base, inner and outer perianths, all segments: Attenuate. Margin, inner perianth, all segments: Entire. Margin, outer perianth, all segments: Entire. Texture, inner and outer perianths, all segments: Smooth, glabrous. Color, inner perianth: When opening, lateral segments, upper surface: 151B; towards the apex and base, 37D. When opening, median segment, upper surface: 1B; towards the apex and base, 37D. When opening, lateral segments, lower surface: Towards the apex, 38A; towards the base, 38B; central spot, 1B. When opening, median segment, lower surface: Towards the apex and base, 38D; mid-section, 151B. Fully opened, lateral and median segments, upper surface: 9A; towards the apex and base, 38C; towards the margins, close to 38D; colors becoming closer to 7A and 51D and towards the margins, close to 50D, respectively, with development. Fully opened, lateral and median segments, lower surface: 2B; towards the apex and base, 38C. Color, outer perianth: When opening, lateral and median segments, upper surface: 51B; towards the margins, 158A. When opening, lateral and median segments, lower surface: 53B. Fully opened, lateral segments, upper surface: 51C. Fully opened, median segment, upper surface: 51C; towards the margins, close to 50D; spots, purplish or 4B to 7B. Fully opened, lateral segments, lower surface: Towards the base, 51D; towards the apex and margins, 50D; tip, 144A. Fully opened, median segment, lower surface: Towards the base, 51C; towards the apex, 50D; tip, 144A.

*Pedicels.*—Length: About 1.1 to 4.1 cm. Diameter: About 1.5 to 2 mm. Strength: Strong. Angle: About 20 to 25° from vertical. Texture: Smooth, glabrous. Color: 147B; towards the apex, 200A with spots, 138B.

*Reproductive organs.*—Stamens: Quantity per flower: Six. Anther shape: Oval. Anther length: About 0.7 mm. Anther diameter: About 0.3 mm. Anther color: 152B. Pollen amount: Abundant. Pollen color: 189A. Pistils: Quantity per flower: One. Pistil length: About 4 cm. Style length: About 3.7 cm. Style color: 54C. Stigma color: 54C. Ovary color: 200A.

*Fruit.*—Shape: Globular. Length: About 2 cm. Diameter: About 1.6 cm. Color: 199A.

*Seed.*—Quantity per fruit: Occasionally one. Length: About 2.5 mm. Diameter: About 2.5 mm. Color: 165B.

Disease/pest resistance: Plants of the new *Alstroemeria* have not been observed to be resistant to pathogens and pests common to *Alstroemerias.*

Temperature tolerance: Plants of the new *Alstroemeria* have been observed to tolerate temperatures from 0 to 40° C.

It is claimed:

1. A new and distinct cultivar of *Alstroemeria* plant named 'Koserin', as illustrated and described.

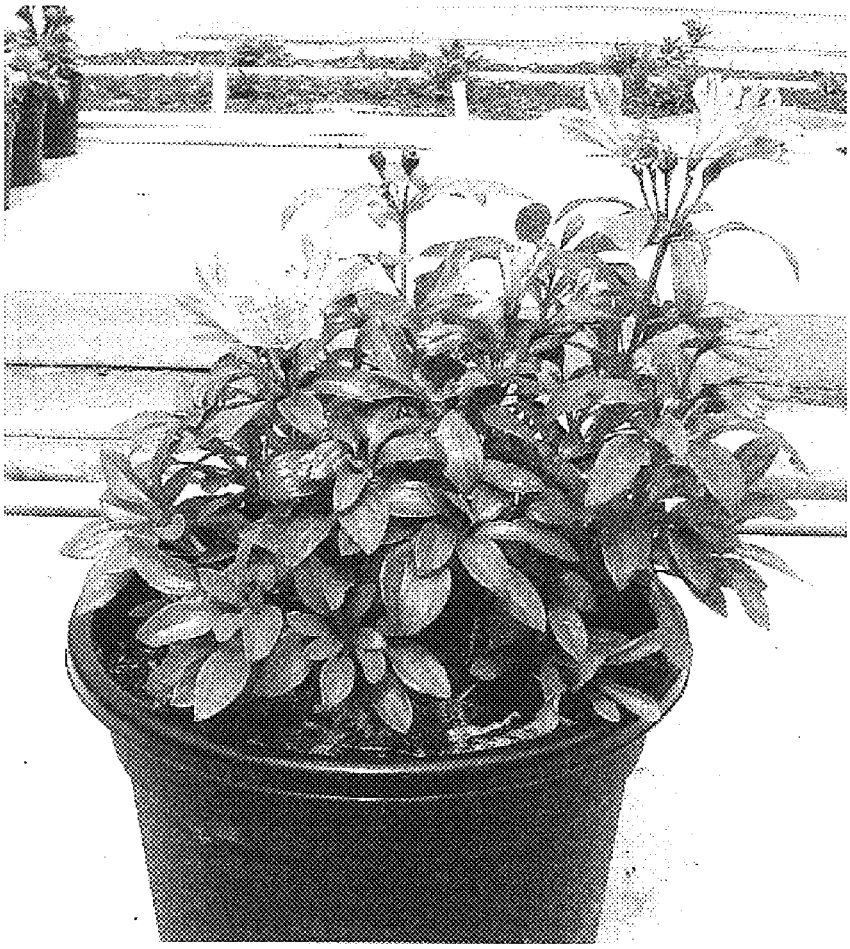

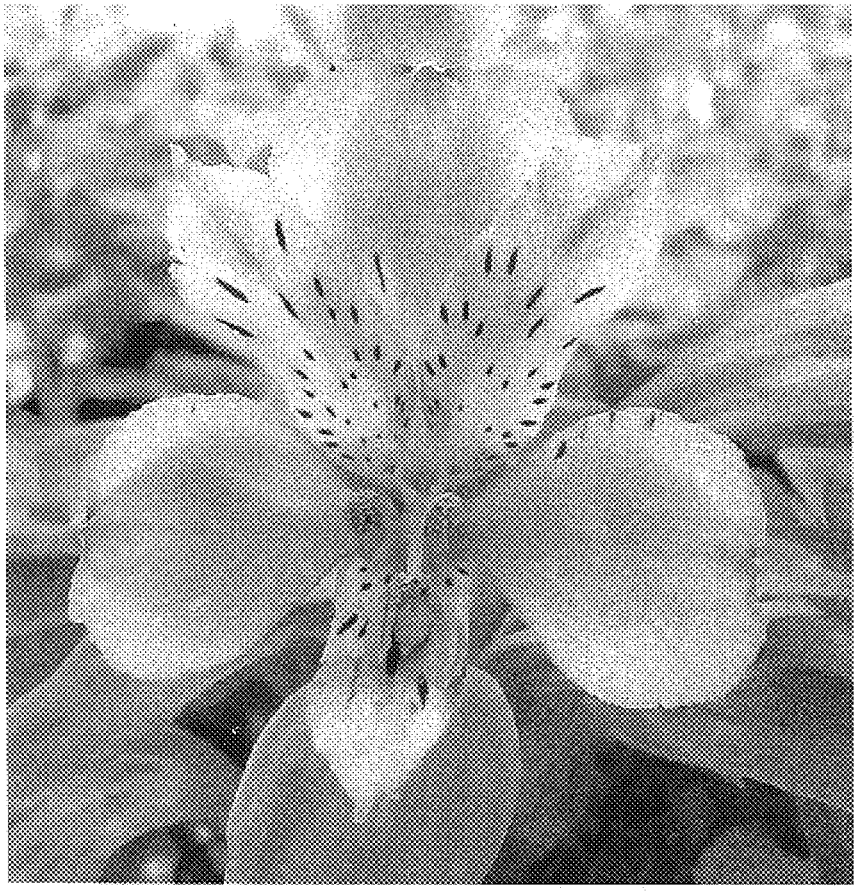

* * * * *